United States Patent
Kweon et al.

(10) Patent No.: US 12,211,250 B2
(45) Date of Patent: Jan. 28, 2025

(54) METHOD AND APPARATUS FOR PROCESSING VASCULAR IMAGE BASED ON BLOOD VESSEL SEGMENTATION

(71) Applicant: MEDIPIXEL, INC., Seoul (KR)

(72) Inventors: Jihoon Kweon, Seoul (KR); Kyo Seok Song, Seoul (KR); Hwi Kwon, Seoul (KR); Se Yeong Park, Seoul (KR); Young-Hak Kim, Seoul (KR); Jee One Park, Seoul (KR); Young In Kim, Seoul (KR); Wan Yeong Kim, Seoul (KR); Yoo Jung Kim, Seoul (KR); Yun Hee Lee, Seoul (KR)

(73) Assignee: MEDIPIXEL, INC., Seoul (KR)

( * ) Notice: Subject to any disclaimer, the term of this patent is extended or adjusted under 35 U.S.C. 154(b) by 0 days.

(21) Appl. No.: 17/922,883

(22) PCT Filed: Dec. 8, 2021

(86) PCT No.: PCT/KR2021/018497
§ 371 (c)(1),
(2) Date: Nov. 2, 2022

(87) PCT Pub. No.: WO2023/277283
PCT Pub. Date: Jan. 5, 2023

(65) Prior Publication Data
US 2024/0221355 A1    Jul. 4, 2024

(30) Foreign Application Priority Data

Jul. 1, 2021    (KR) .......................... 10-2021-0086439

(51) Int. Cl.
*G06V 10/764*    (2022.01)
*G06V 10/22*    (2022.01)
(Continued)

(52) U.S. Cl.
CPC ............ *G06V 10/764* (2022.01); *G06V 10/22* (2022.01); *G06V 10/273* (2022.01); *G06V 10/98* (2022.01); *G16H 30/40* (2018.01); *G06V 2201/03* (2022.01)

(58) Field of Classification Search
CPC .... G06V 10/22; G06V 10/273; G06V 10/764; G06V 10/98; G06V 2201/03;
(Continued)

(56) References Cited

U.S. PATENT DOCUMENTS

2017/0140532 A1\*   5/2017   Dascal ................. G06T 7/0012
2017/0262733 A1\*   9/2017   Gulsun ............... G06V 10/454
(Continued)

FOREIGN PATENT DOCUMENTS

JP    2017-060682 A    3/2017
JP    2018-202163 A    12/2018
(Continued)

OTHER PUBLICATIONS

Zhao et al., "Intracranial Vascular Structure Extraction: A Machine Learning Approach", IEEE Access, vol. 7, 2019, pp. 100933-100942 (Year: 2019).\*

(Continued)

*Primary Examiner* — Ping Y Hsieh
*Assistant Examiner* — Jose M Torres
(74) *Attorney, Agent, or Firm* — BOND, SCHOENECK & KING, PLLC; George R. McGuire

(57) ABSTRACT

A vascular image processing method performed by a processor includes extracting, from a vascular image, a first vascular region corresponding to an entire blood vessel included in the vascular image, a second vascular region corresponding to a target vessel and one or more branch vessels connected to the target vessel, and a third vascular region corresponding to the target vessel, and predicting a (Continued)

vascular structure in the vascular image, based on the first vascular region, the second vascular region, and the third vascular region, which are extracted from the vascular image.

15 Claims, 9 Drawing Sheets

(51) Int. Cl.
  *G06V 10/26* (2022.01)
  *G06V 10/98* (2022.01)
  *G16H 30/40* (2018.01)

(58) Field of Classification Search
  CPC ........ G16H 20/40; G16H 30/40; G16H 50/20; G16H 50/70; G06T 7/0012; G06T 7/11; G06T 7/194; G06T 2207/10088; G06T 2207/10116; G06T 2207/20081; G06T 2207/20084; G06T 2207/30048; G06T 2207/30101; A61B 6/481; A61B 6/504; A61B 6/5217
  See application file for complete search history.

(56) References Cited

U.S. PATENT DOCUMENTS

2018/0235561 A1* 8/2018 Lavi .................. G16H 50/30
2021/0166392 A1* 6/2021 Kaethner .............. G06T 7/0016
2021/0169349 A1* 6/2021 Madabhushi ........ A61B 5/7275

FOREIGN PATENT DOCUMENTS

| JP | 2019-521733 A | 8/2019 |
| JP | 2019-193808 A | 11/2019 |
| KR | 10-2014-0015964 A | 2/2014 |

OTHER PUBLICATIONS

EP Search Report, Application No. 21935454.5, dated Sep. 27, 2023, pp. 1-10.

Charnoz, Arnaud, et al., "Tree Matching Applied to Vascular System", Graph-Based Representations in Pattern Recognition, Jan. 1, 2005, vol. 3434, Springer Berlin Heidelberg, Germany, XP093040968, ISSN: 0302-9743, ISBN: 978-3-540-31988-7, pp. 183-192, DOI: 10.1007/978-3-540-31988-7_17, Retrieved from the Internet: URL: https://link.springer.com/content/pdf/10.1007/978-3-540-31988-7_17.pdf?pdf=inline%20link>.

Moccia, Sara, et al., "Blood vessel segmentation algorithms— Review of methods, datasets and evaluation metrics", Computer Methods and Programs in Biomedicine, Elsevier, Amsterdam, NL, vol. 158, Feb. 10, 2018, XP085359769, ISSN: 0169-2607, DOI: 10.1016/J.CMPB.2018.02.001, pp. 71-91.

International Search Report and Written Opinion.

* cited by examiner

METHOD AND APPARATUS FOR PROCESSING VASCULAR IMAGE BASED ON BLOOD VESSEL SEGMENTATION

CROSS-REFERENCE TO RELATED APPLICATION(S)

This application is the United States National Phase application filed under 35 U.S.C. 371 of International Application No. PCT/KR2021/018497, filed Dec. 8, 2021 which claims priority to Korean Patent Application No. 10-2021-0086439 filed with the Korean Patent Office on Jul. 1, 2021, the entirety of each of which is hereby incorporated by reference.

TECHNICAL FIELD

The following description relates to a method of processing a vascular image based on blood vessel segmentation.

BACKGROUND ART

To treat cardiovascular, cerebrovascular, and peripheral blood vessels, an interventional procedure, such as stent insertion, has been widespread. Before performing the procedure, the severity of a lesion of a patient may be evaluated by an image through cardiac angiography. To quantitatively evaluate the severity of a lesion, information on blood vessels may be required and for this, research into blood vessel segmentation has been continuously conducted. Blood vessel segmentation information may be variously used for extracting a centerline, measuring a branch angle, and predicting a position of a lesion. Recently, a deep learning-based blood vessel segmentation method has been developed and may have better performance compared to the conventional method.

The conventional vascular region analysis method has adopted binary segmentation into a vascular region and a non-vascular region. In the conventional method, when vascular regions overlap with each other, the connectivity may be unclear, and thus, a vascular tree structure may be difficult to be identified. When the analysis on the vascular tree structure is incorrect, the accuracy of determining which blood vessel is divided may deteriorate. In addition, when the vascular tree structure is incorrectly analyzed, a lesion may be misidentified by using a blood vessel that is not actually connected and an error may occur in the application of a syntax score that assigns different scores to each vascular unit and performs diagnosis. Therefore, an accurate analysis on the vascular tree structure is required. Furthermore, to navigate a surgical tool, the vascular tree structure may need to be accurately analyzed.

DISCLOSURE OF THE INVENTION

Technical Solutions

According to an aspect, there is provided a vascular image processing method performed by a processor including extracting, from a vascular image, a first vascular region corresponding to an entire blood vessel included in the vascular image, a second vascular region corresponding to a target vessel and one or more branch vessels connected to the target vessel, and a third vascular region corresponding to the target vessel, and predicting a vascular structure in the vascular image, based on the first vascular region, the second vascular region, and the third vascular region, which are extracted from the vascular image.

The predicting of the vascular structure includes classifying each point corresponding to a blood vessel in the vascular image into the target vessel, the one or more branch vessels connected to the target vessel, and a separate vessel disconnected from the target vessel.

The predicting of the vascular structure includes predicting a region corresponding to the target vessel in the vascular image by overlapping the first vascular region, the second vascular region, and the third vascular region with each other.

The extracting includes extracting the first vascular region prior to extraction of the second vascular region and the third vascular region, extracting, from the first vascular region, a cross region including at least one of a region comprising a branch point where a branch vessel branches off and a region where different blood vessels overlap with each other, and extracting the second vascular region and the third vascular region from the vascular image, based on the extracted cross region.

The vascular image processing method further includes correcting an error of a predicted vascular structure in the vascular image.

The correcting of the error of the predicted vascular structure includes obtaining another vascular image captured at a different time from the vascular image, and correcting the error of the predicted vascular structure in the vascular image, based on a comparison result of the predicted vascular structure in the vascular image and a predicted vascular structure in the other obtained vascular image.

The correcting of the error of the predicted vascular structure includes correcting the error of the predicted vascular structure based on at least one or a combination of two or more of a diameter of a target vessel obtained from the predicted vascular structure, an endpoint direction of the target vessel obtained from the predicted vascular structure, and lesion information.

The correcting of the error of the predicted vascular structure includes correcting the error of the predicted vascular structure in the vascular image, based on a candidate separate vessel region generated by removing a region corresponding to the second vascular region from the first vascular region and a candidate branch vessel region generated by removing a region corresponding to the third vascular region from the second vascular region.

According to another aspect, there is provided a vascular image processing apparatus including an image obtainer configured to obtain a vascular image, and a processor configured to extract, from the vascular image, a first vascular region corresponding to an entire blood vessel included in the vascular image, a second vascular region corresponding to a target vessel and one or more branch vessels connected to the target vessel, and a third vascular region corresponding to the target vessel and predict a vascular structure in the vascular image, based on the first vascular region, the second vascular region, and the third vascular region, which are extracted from the vascular image.

Effects

A vascular image processing apparatus according to an example embodiment may extract vascular regions by dividing a phase into a target vessel, a branch vessel connected to the target vessel, and a separate vessel disconnected from the target vessel and may more accurately predict a vascular structure by combining the extraction results.

A vascular image processing apparatus according to an example embodiment may solve a difficulty in predicting a vascular structure caused by overlapping of blood vessels by dividing a vascular image by assigning a different phase to a blood vessel.

BEST MODE FOR CARRYING OUT THE INVENTION

Figure 1:
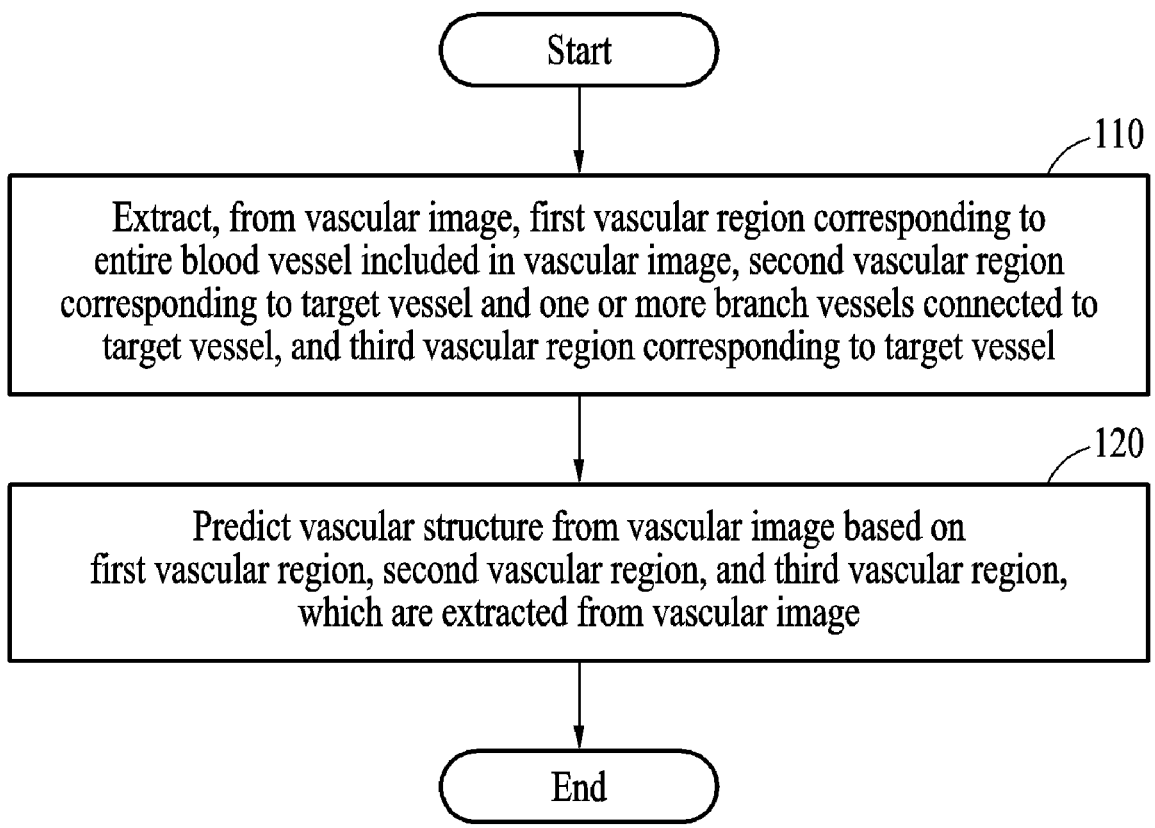
FIG. 1 is a flowchart illustrating a method of processing a vascular image, according to an example embodiment.

The following detailed structural or functional description is provided as an example only and various alterations and modifications may be made to the examples. Here, the examples are not construed as limited to the disclosure and should be understood to include all changes, equivalents, and replacements within the idea and the technical scope of the disclosure.

Terms, such as first, second, and the like, may be used herein to describe components. Each of these terminologies is not used to define an essence, order or sequence of a corresponding component but used merely to distinguish the corresponding component from other component(s). For example, a first component may be referred to as a second component, and similarly the second component may also be referred to as the first component.

It should be noted that if it is described that one component is "connected", "coupled", or "joined" to another component, a third component may be "connected", "coupled", and "joined" between the first and second components, although the first component may be directly connected, coupled, or joined to the second component.

The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Hereinafter, example embodiments will be described in detail with reference to the accompanying drawings. When describing the embodiments with reference to the accompanying drawings, like reference numerals refer to like elements and a repeated description related thereto will be omitted.

FIG. 1 is a flowchart illustrating a method of processing a vascular image, according to one embodiment.

In operation 110, a vascular image processing apparatus may extract, from a blood vessel image (hereinafter, also referred to as a vascular image), a first vascular region corresponding to the entire blood vessel included in the vascular image, a second vascular region corresponding to a target vessel and one or more branch vessels connected to the target vessel, and a third vascular region corresponding to the target vessel.

The entire blood vessel included in the vascular image may include the target vessel, one or more branch vessels, and a separate vessel. The target vessel may represent a major vessel. The branch vessel may represent a blood vessel directly or indirectly connected to the target vessel and branching off from the target vessel. The separate vessel may represent a separate blood vessel disconnected from the target vessel. For example, the vascular image may represent an image capturing a left coronary artery (LCA). The LCA may be divided into a left anterior descending (LAD) and a left circumflex artery (LCX). When the target vessel represents the major vessel in the LAD, the separate vessel may represent the LCX.

The vascular image processing apparatus according to one embodiment may obtain a vascular image captured by a vascular image capturing device. The vascular image may be an image that captures blood vessels of a living body and may be obtained by using a coronary angiography (hereinafter, referred to as CAG) image and/or a magnetic resonance imaging (hereinafter, referred to as MRI). For example, the vascular image may be an image obtained by performing X-ray imaging on a living body into which a contrast medium is injected.

According to one embodiment, the vascular image processing apparatus may extract the first vascular region, the second vascular region, and the third vascular region from a vascular image based on a machine learning model. The machine learning model may be at least one model including a machine learning structure configured to extract a vascular region from a vascular image in response to an input of the vascular image, and for example, may include a neural network. The vascular image processing apparatus may calculate an extraction result of the vascular region by performing an operation on the obtained vascular image based on the machine learning model described above.

The vascular image processing apparatus may selectively use a machine learning model to extract the target vessel among a plurality of machine learning models based on the shape and type of blood vessel, and/or a vascular region. The target vessel may be a blood vessel to be extracted as a vascular image, for example, may be one of the entire blood vessel included in the vascular image, the major vessel and the branch vessel connected to the major vessel, and the major vessel. However, the target vessel is not limited thereto. According to one embodiment, the vascular image processing apparatus may store a plurality of machine learning models based on the target vessel. For example, the vascular image processing apparatus may select the target vessel to be extracted and may load a machine learning model corresponding to the selected target vessel. The vascular image processing apparatus may generate an extraction result of the target vessel from the vascular image by using the loaded machine learning model. The machine learning models may have different trained parameters, and furthermore, may have different machine learning structures (e.g., a convolutional neural network, a U-net structure, and the like).

For example, the vascular image processing apparatus may extract the first vascular region by using a machine learning model trained to extract, from a vascular image, the entire blood vessel included in the vascular image. The vascular image processing apparatus may extract the second vascular region by using a machine learning model trained to extract, from a vascular image, a target vessel (e.g., a major vessel) and a branch vessel connected to the target vessel. The vascular image processing apparatus may extract the third vascular region by using a machine learning model trained to extract the target vessel from a vascular image.

For example, output data of the machine learning model may include information on a score corresponding to a possibility (e.g., a probability) of indicating a target vessel (e.g., the entire blood vessel, a major vessel, and the like) for each point from a plurality of points in the vascular image. Here, the target vessel may represent a blood vessel (e.g., the entire blood vessel, the major vessel, or the major vessel and the branch vessel connected to the major vessel) to be extracted by the corresponding machine learning model. The vascular image processing apparatus may generate an extraction result by determining a point having a score that is equal to or greater than a threshold value in the output data to be a region corresponding to the target vessel. In another example, the output data of the machine learning model may be a vascular region segmented from the vascular image and may include a point extracted as a target vessel among a plurality of points in the vascular image. The extraction result of the target vessel may be, for example, an image of a set of points, which are extracted to be the target vessel among points in the vascular image and/or an image of a region that is segmented from the vascular image and corresponds to the target vessel.

In addition, the neural network may include a deep neural network (DNN). The DNN may include a fully connected network (FCN), a deep convolutional network (DCN), and a recurrent neural network (RNN). The neural network maps, based on deep learning, input data and output data that are in a non-linear relationship, to perform, for example, object classification, object recognition, speech recognition or radar image recognition. Deep learning may be a machine learning scheme to solve a problem, such as object recognition from a large data set, and through supervised or unsupervised learning, input data and output data may be mapped to each other. In case of supervised learning, the machine learning model described above may be trained based on training data including a pair of a training input (e.g., a vascular image for training) and a training output mapped to the training input (e.g., a ground truth image obtained by segmenting the vascular image for training into the target vessel by an expert). For example, the machine learning model may be trained to output a training output from a training input. A machine learning model in training (hereinafter, referred to as a 'temporary model') may generate a temporary output in response to the training input and may be trained to minimize a loss between the temporary output and a training output (e.g., a ground truth value). During the training process, a parameter (e.g., a connection weight between nodes and layers in the neural network) of the machine learning model may be updated based on the loss.

Then, in operation 120, the vascular image processing apparatus may predict a vascular structure in the vascular image based on the first vascular region, the second vascular region, and the third vascular region, which are extracted from the vascular image. Prediction of the vascular structure may represent classification for each point corresponding to the blood vessel in the vascular image. The vascular image processing apparatus may classify each point corresponding to the blood vessel in the vascular image into the target vessel, at least one branch vessel connected to the target vessel, and the separate vessel disconnected from the target vessel. The vascular image processing apparatus may more accurately predict the vascular structure by predicting a vascular region by dividing a phase in the vascular image into the target vessel, the branch vessel connected to the target vessel, and the separate vessel disconnected from the target vessel. Hereinafter, a method of predicting a vascular structure based on the first vascular region, the second vascular region, and the third vascular region is described.

Figure 2A:
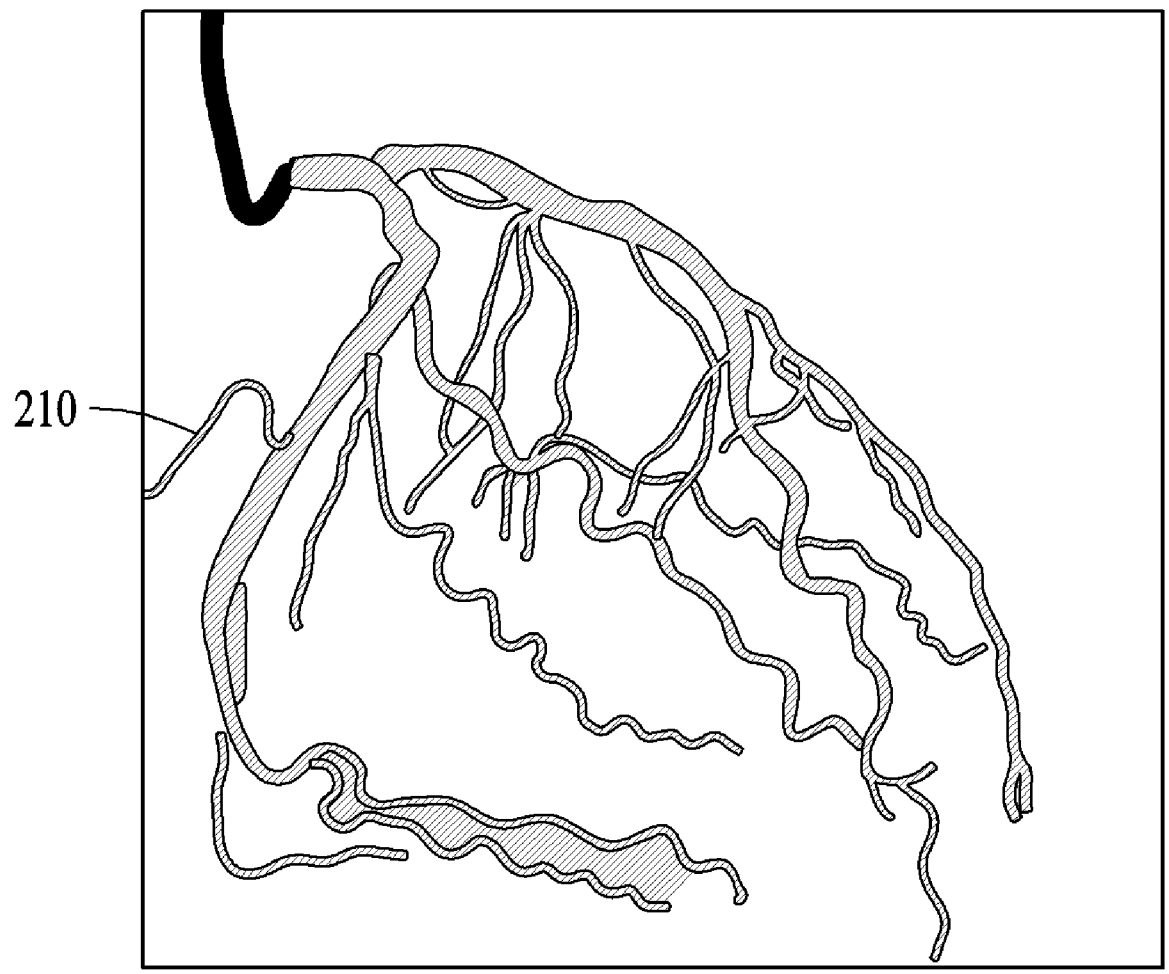
FIGS. 2A to 2C are diagrams displaying a vascular region extracted by a vascular image processing apparatus according to an example embodiment.
Figure 2B:
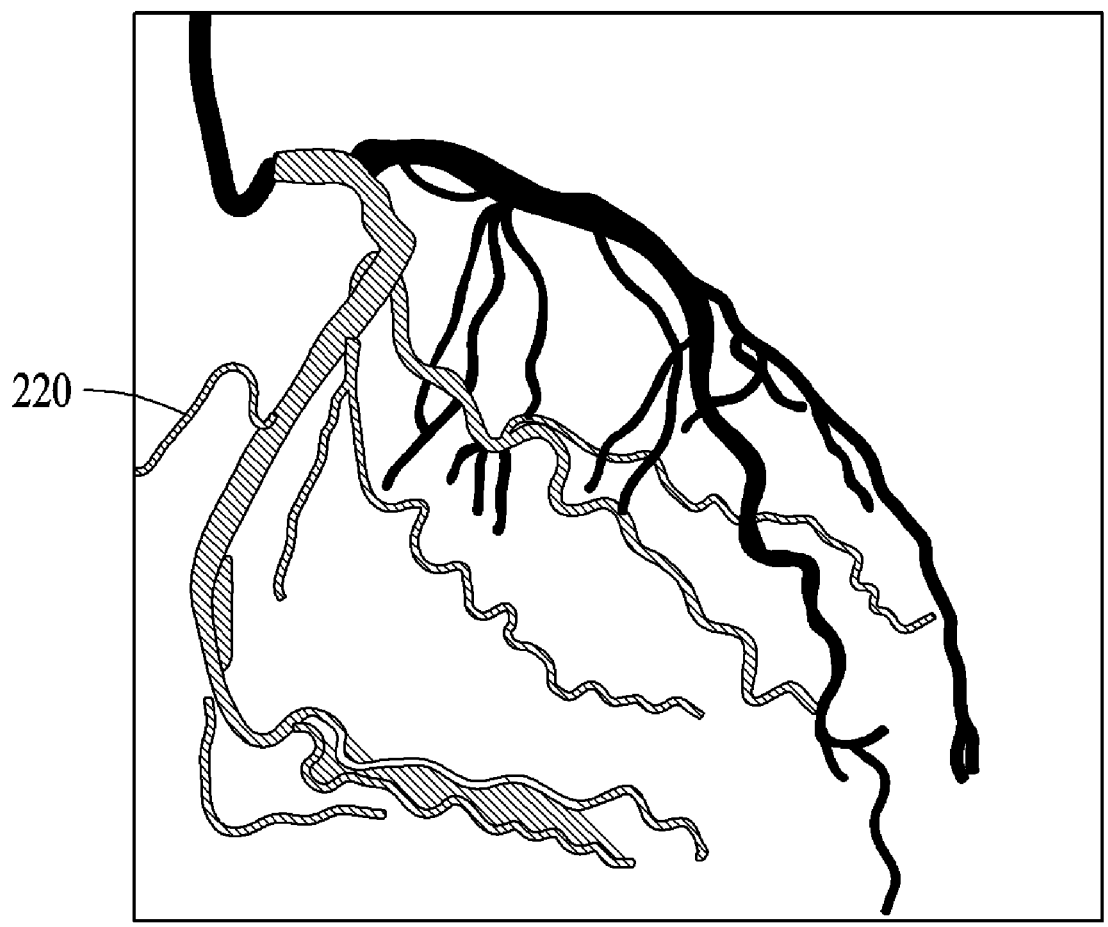
Figure 2C:
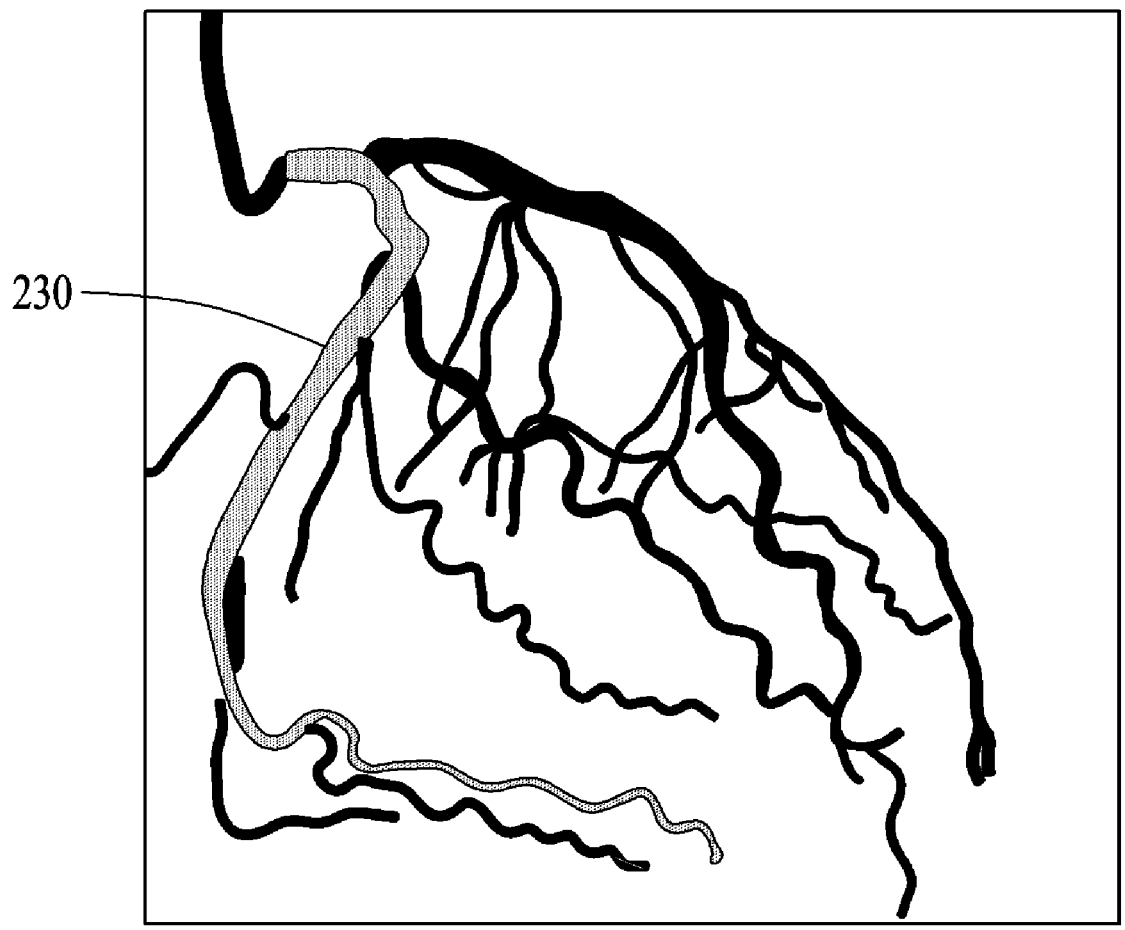

FIGS. 2A to 2C are diagrams displaying a vascular region extracted by a vascular image processing apparatus according to one embodiment.

The vascular image processing apparatus may obtain a vascular image 200 captured by a vascular image capturing device.

Referring to FIG. 2A, the vascular image processing apparatus may extract, from the vascular image 200, a first vascular region 210 corresponding to the entire blood vessel included in the vascular image. The entire blood vessel included in the vascular image may include a target vessel, a branch vessel connected to the target vessel, and a separate vessel disconnected from the target vessel.

Referring to FIG. 2B, the vascular image processing apparatus may extract, from the vascular image 200, a second vascular region 220 corresponding to the target vessel and at least one branch vessel connected to the target vessel. For example, the target vessel may be a major vessel. The branch vessel connected to the target vessel may include a branch vessel branching off from the target vessel and directly connected to the target vessel as well as a branch vessel branching off from the target vessel and then, branching off again from the branch vessel. The branch vessel connected to the target vessel may include a branch vessel indirectly connected along the target vessel.

Referring to FIG. 2C, the vascular image processing apparatus may extract a third vascular region 230 corresponding to the target vessel from the vascular image 200.

According to one embodiment, the vascular image processing apparatus may predict a vascular structure in the vascular image based on the first vascular region 210, the second vascular region 220, and the third vascular region 230, which are extracted from the vascular image 200. The vascular image processing apparatus may classify each point corresponding to the blood vessel in the vascular image into the target vessel, at least one branch vessel connected to the target vessel, and the separate vessel disconnected from the target vessel. The vascular image processing apparatus may predict a region corresponding to the target vessel, a region corresponding to the branch vessel connected to the target vessel, and a region corresponding to the separate vessel disconnected from the target vessel in the vascular image, based on the first vascular region, the second vascular region, and the third vascular region. Here, the separate vessel disconnected from the target vessel may refer to a blood vessel that is not directly or indirectly connected to the target vessel and may represent a blood vessel disconnected from the target vessel. For example, the separate vessel disconnected from the target vessel may represent a blood vessel branching off from a starting point of the blood vessel in a direction different from the target vessel.

Figure 3:
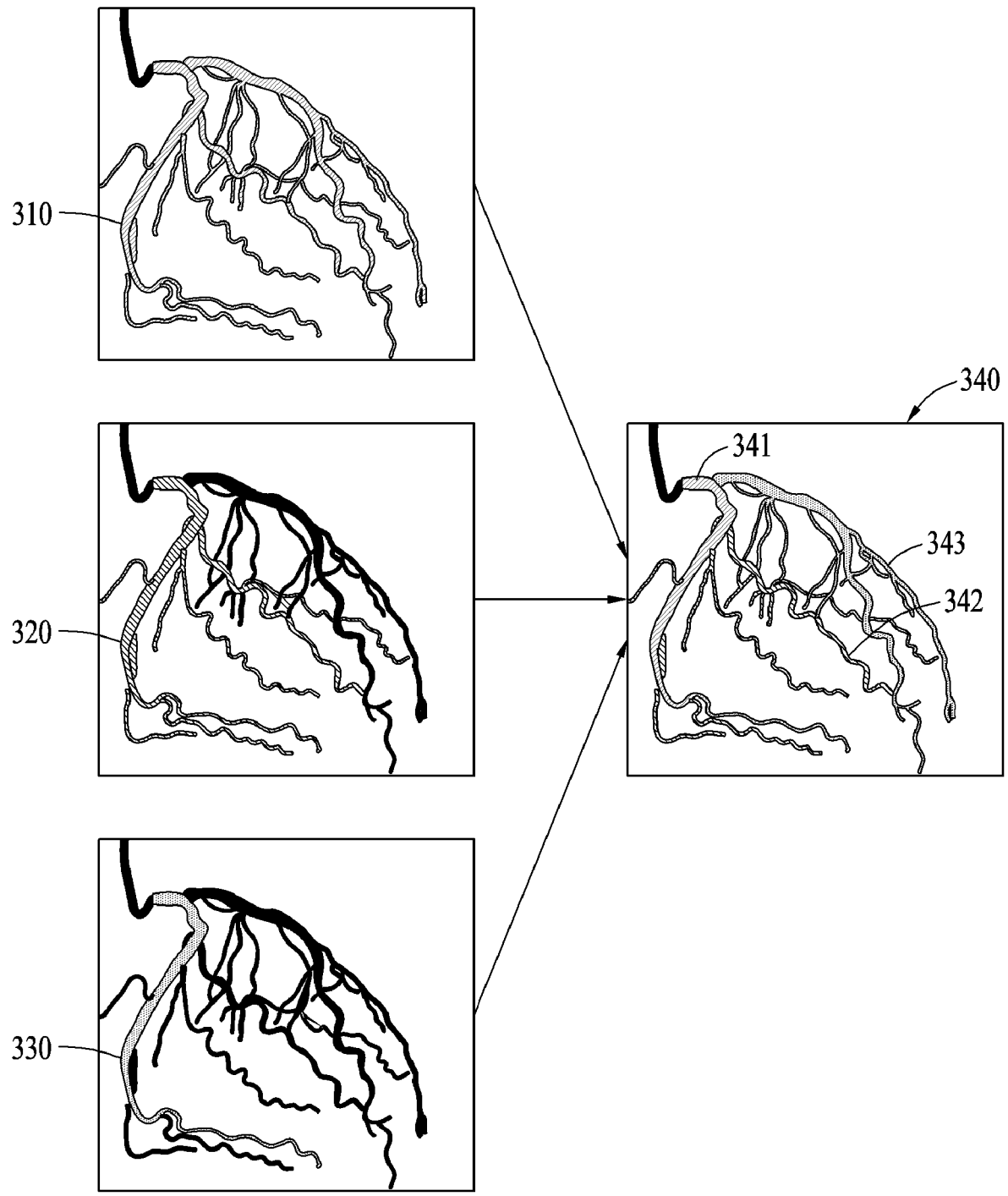
FIG. 3 is a diagram illustrating an operation of a vascular image processing apparatus to predict a vascular structure of a vascular image, according to an example embodiment.

FIG. 3 is a diagram illustrating an operation of a vascular image processing apparatus to predict a vascular structure of a vascular image, according to one embodiment.

In one embodiment, the vascular image processing apparatus may predict a vascular structure in a vascular image 340 by ensembling a result on a first vascular region 310, a second vascular region 320, and a third vascular region 330, which are extracted from the vascular image.

According to one embodiment, the vascular image processing apparatus may predict a region 341 corresponding to the target vessel in the vascular image, based on the first vascular region 310, the second vascular region 320, and the third vascular region 330, which are extracted from the vascular image. Furthermore, the vascular image processing apparatus may predict a region 342 corresponding to the at least one branch vessel connected to the target vessel and a region 343 corresponding to the separate vessel disconnected from the target vessel in the vascular image, based on the first vascular region 310, the second vascular region 320, and the third vascular region 330, which are extracted from the vascular image. The vascular image processing apparatus may improve the accuracy of predicting the vascular structure in the vascular image by ensembling the first vascular region 310, the second vascular region 320, and the third vascular region 330.

Hereinafter, some embodiments that the vascular image processing apparatus predicts a region corresponding to the target vessel based on the first vascular region 310, the second vascular region 320, and the third vascular region 330 are provided.

According to one embodiment, the vascular image processing apparatus may predict a region corresponding to the target vessel in the vascular image by overlapping the first vascular region 310, the second vascular region 320, and the third vascular region 330. The first vascular region and the second vascular region may extract regions including the region corresponding to the target vessel, and the third vascular region may extract the region corresponding to the target vessel. According, the vascular image processing apparatus may predict the region corresponding to the target vessel in the vascular image by ensembling the first vascular region, the second vascular region, and the third vascular region. For example, the vascular image processing apparatus may determine the region corresponding to the target vessel to be an overlapping region between the third vascular region 330 and the second vascular region 320. For example, the vascular image processing apparatus may determine the region corresponding to the target vessel to be an overlapping region between the third vascular region 330 and the first vascular region 310. For example, the vascular image processing apparatus may determine the region corresponding to the target vessel by comparing the overlapping region between the third vascular region 330 and the second vascular region 320 to the overlapping region between the third vascular region 330 and the first vascular region 310. However, the method of predicting a region corresponding to a target vessel is not limited thereto, and the region corresponding to the target vessel may be predicted by various methods by overlapping extracted vascular regions.

According to one embodiment, the vascular image processing apparatus may divide the region corresponding to the target vessel from the first vascular region 310. The vascular image processing apparatus may divide the region corresponding to the target vessel from the second vascular region 320. The vascular image processing apparatus may predict the region 341 correspond to the target vessel in the vascular image based on a combination of two or more of a divided region corresponding to the target vessel from the first vascular region 310, a divided region corresponding to the target vessel from the second vascular region 320, and a divided region corresponding to the target vessel from the third vascular region 330. For example, the vascular image processing apparatus may divide the region corresponding to the target vessel from the first vascular region 310 through image processing. Since the first vascular region is a region including the target vessel, the branch vessel connected to the target vessel, and a separate vessel disconnected from the target vessel, another image processing may be required to divide the region corresponding to the target vessel from the first vascular region. Similarly, since the second vascular region is a region including the target vessel and the branch vessel connected to the target vessel, the region corresponding to the target vessel may be divided from the second vascular region through image processing.

The vascular image processing apparatus may assign a score of '1' to a point corresponding to a target vessel region divided from the first vascular region among points included in the vascular image and may assign a score of '0' to the remaining points. Similarly, the vascular image processing apparatus may assign a score of '1' to a point corresponding to the target vessel region extracted from the second vascular region and may assign a score of '0' to the remaining points. The vascular image processing apparatus may assign a score of '1' to a point corresponding to the third vascular region and may assign a score of '0' to the remaining points. For example, the vascular image processing apparatus may calculate an average of three scores assigned to the points in the vascular image and may determine a point that is included in the target vessel to be a point having an average score that exceeds a threshold score (for example, 0.5). For example, the vascular image processing apparatus may determine that only a point where all three assigned scores are '1' is the point included in the target vessel.

The vascular image processing apparatus may assign, to a point, a score corresponding to a possibility (for example, a probability) of indicating the target vessel from the extraction result of the first vascular region. Similarly, the vascular image processing apparatus may assign a score corresponding to the possibility of indicating the target vessel to each point from the extraction result of the second vascular region and the extraction result of the third vascular region. Then, the vascular image processing apparatus may calculate an average of three scores assigned to points included in the vascular image and may determine the point included in the target vessel to be a point having an average score that exceeds the threshold score.

Figure 4:
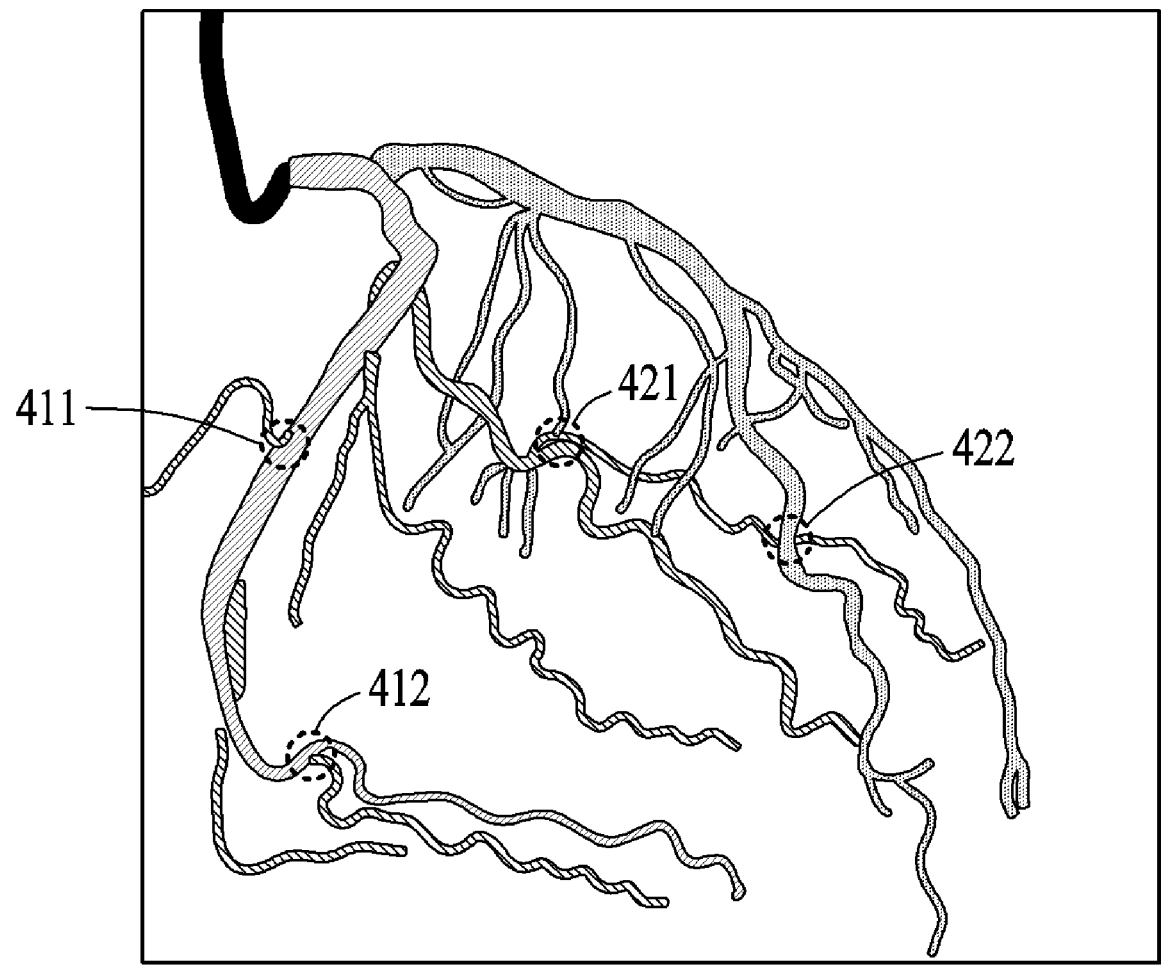
FIG. 4 is a diagram illustrating an operation of a vascular image processing apparatus to extract a second vascular region and a third vascular region based on a cross region extracted from a first vascular region, according to an example embodiment.

FIG. 4 is a diagram illustrating an operation of a vascular image processing apparatus to extract a second vascular region and a third vascular region based on a cross region extracted from a first vascular region, according to one embodiment.

The vascular image processing apparatus may extract a first vascular region from a vascular image 400 prior to extracting a second vascular region and a third vascular region. The vascular image processing apparatus may extract a cross region including at least one of regions 411 and 412 including branch points where branch vessels branch off from the first vascular region and regions 421 and 422 where different blood vessels overlap with each other. The vascular image processing apparatus may extract the second vascular region and the third vascular region from the vascular image, based on the extracted cross region.

More specifically, the vascular image processing apparatus may extract, from the vascular image 400, the first vascular region with respect to the entire blood vessel included in the vascular image. The first vascular region may represent a region including the target vessel, the branch vessel connected to the target vessel, and the separate vessel disconnected from the target vessel. The vascular image processing apparatus may extract the cross region from the first vascular region. The cross region may include an overlapping region between a region including a branch point of the branch vessel and a region where different blood vessels overlap with each other. The branch point of the branch vessel may represent a point where two or more branch vessels are combined and/or where a vessel is divided into a plurality of branch vessels. A vascular region corresponding to a blood vessel included in the vascular image 400 may have a plurality of branch points. The region where different blood vessels overlap with each other may represent an overlapping region, appeared on the vascular image, between the target vessel and the separate vessel disconnected from the target vessel. Since the vessel image 400 is a two-dimensional irradiation image obtained by irradiating an X-ray to a three-dimensional blood vessel, a predetermined blood vessel may hide a blood vessel located deeper in the vascular image 400. In other words, the region where different blood vessels overlap with each other may represent a region where a predetermined blood vessel hides another blood vessel due to a depth difference rather than a region where blood vessels penetrate each other.

According to one embodiment, the vascular image processing apparatus may individually extract the first vascular region, the second vascular region, and the third vascular region from the vascular image, but may output the first vascular region, the second vascular region, and the third vascular region in association with each other. The vascular image processing apparatus may extract the second vascular region and the third vascular region from the vascular image, based on the cross region extracted from the first vascular region. For example, the vascular image processing apparatus may input information on the cross region extracted from the first vascular region to a network configured to extract the second vascular region and may more accurately extract the second vascular region from the vascular image by utilizing the information on the cross region input to the network. Similarly, the vascular image processing apparatus may input information on the cross region extracted from the first vascular region to a network configured to extract the third vascular region and may more accurately extract the third vascular region based on the input information. Here, the network may be a network configured to extract a vascular region from a vascular image and may be, for example, a neural network. Furthermore, when the vascular image processing apparatus inputs information on the cross region to a network, the vascular image processing apparatus may divide and input information on a region including a branch point where branch vessels branch off and information on a region where different blood vessels overlap with each other.

Figure 5:
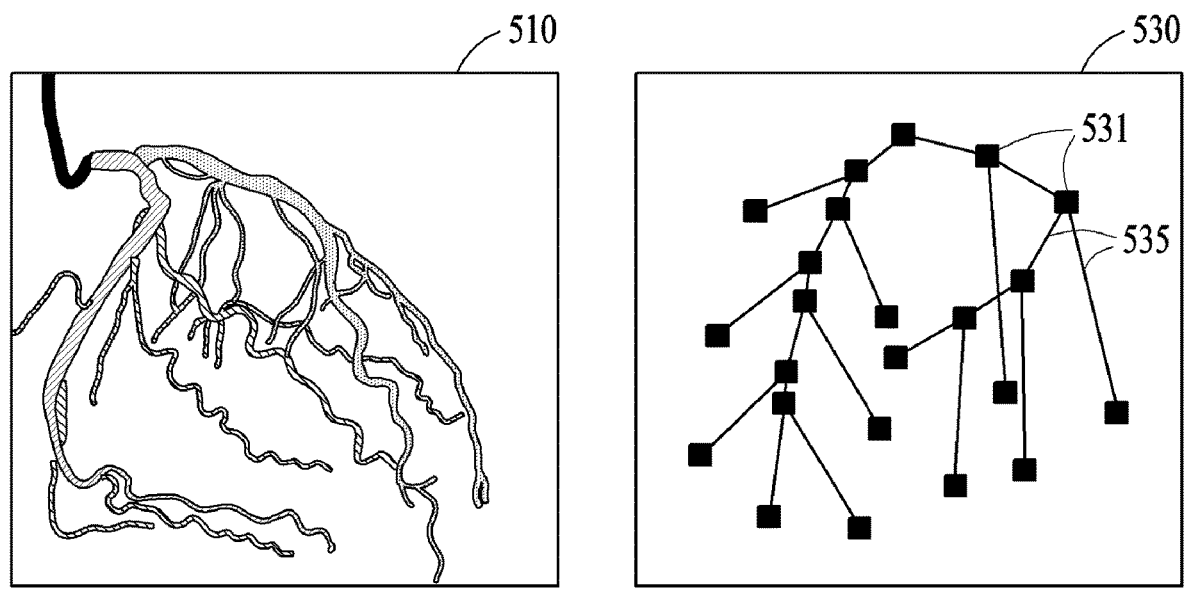
FIGS. 5 to 6 are diagrams illustrating an operation of a vascular image processing apparatus to correct an error of a predicted vascular structure, according to an example embodiment.
Figure 6:
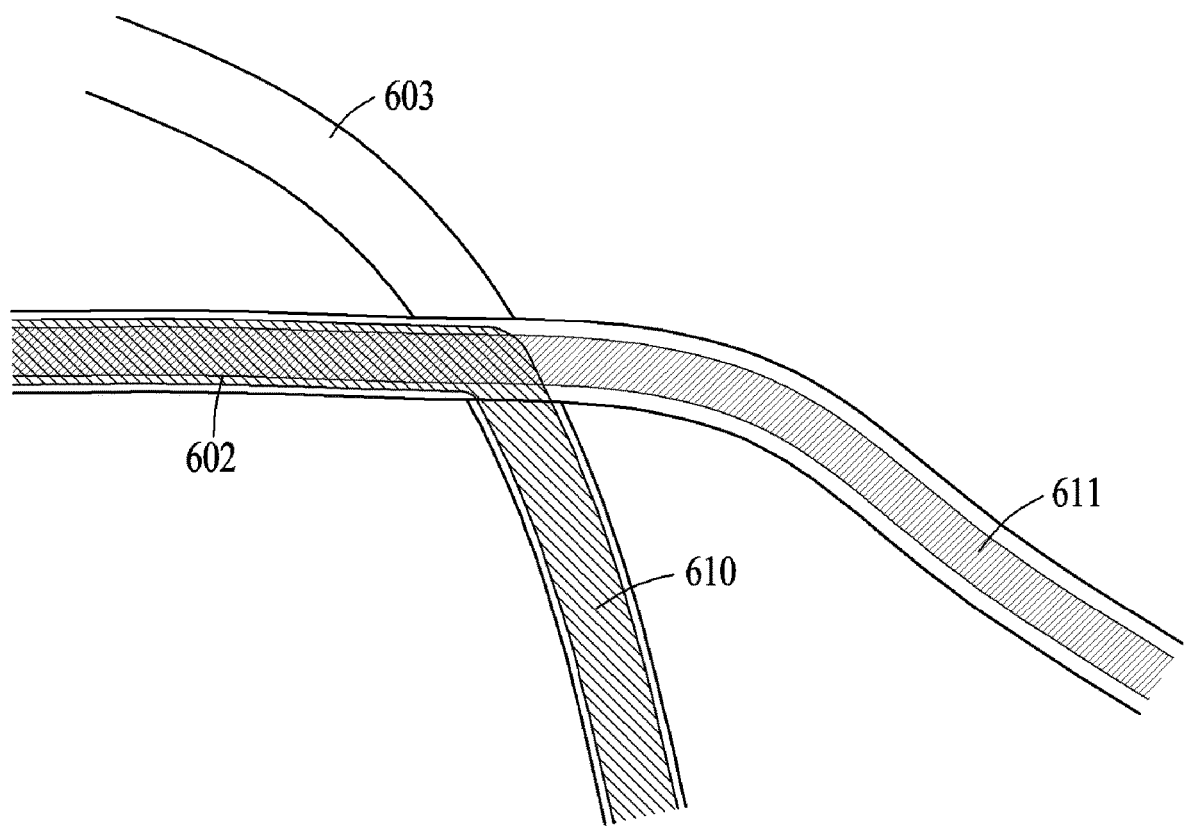

FIGS. 5 to 6 are diagrams illustrating an operation of a vascular image processing apparatus to correct an error of a predicted vascular structure, according to one embodiment.

According to one embodiment, the vascular image processing apparatus may predict a vascular structure of a vascular image by classifying points corresponding to blood vessels in the vascular image into a target vessel, one or more branch vessels connected to the target vessel, and a separate vessel disconnected from the target vessel. The vascular image processing apparatus may correct an error of the predicted vascular structure. For example, the predicted vascular structure of the vascular image processing apparatus may include an error of erroneously classifying a point included in the separate vessel disconnected from the target vessel as a point included in the target vessel. For example, the predicted vascular structure may include an error of erroneously classifying a point included in the branch vessel connected to the target vessel as a point included in the target vessel. In this case, the vascular image processing apparatus may verify the predicted vascular structure by using various methods and may automatically correct a region determined to be an error in the predicted vascular structure. Hereinafter, a description of various methods of the vascular image processing apparatus to correct an error of the predicted vascular structure is provided.

According to one embodiment, the vascular image processing apparatus may correct an error of the predicted vascular structure by using a different vascular image captured at a different time from the existing vascular image (hereinafter, referred to as a 'target vascular image'). The vascular image processing apparatus may obtain the other vascular image captured at a different time from the target vascular image from a vascular image capturing device. The vascular image processing apparatus may obtain one or more vascular images. The vascular image processing apparatus may compare a predicted vascular structure in the target vascular image to a predicted vascular structure in the other vascular images and may correct an error of the predicted vascular structure in the target vascular image based on the comparison result. The vascular image processing apparatus may predict the vascular structure for the other vascular images in a similar manner to the method of predicting a vascular structure in the target vascular image. In other words, the vascular image processing apparatus may extract a vascular region for the entire blood vessel, a vascular region for a target vessel and one or more branch vessels connected to the target vessel, and a vascular region for the target vessel from the other vascular images and may predict a vascular structure for the other vascular images based on the extracted results.

The vascular image processing apparatus may obtain a plurality of other vascular images. The vascular image processing apparatus may output predicted vascular structures for each of the plurality of other vascular images and may compare to the predicted vascular structure of the target vascular image. According to one embodiment, the vascular image processing apparatus may generate a blood vessel tree that represents the vascular structure for each of the other vascular images. Referring to FIG. 5, there is a blood vessel tree 530 generated from a vascular image 510. The blood vessel tree 530 may include branch points 531 and blood vessel lines 535. The vascular image processing apparatus may individually generate a blood vessel tree for the target vascular image and each of the plurality of other vascular images. In the blood vessel tree 530, the target vessel, the branch vessel connected to the target vessel, and the separate vessel disconnected from the target vessel may be separately displayed.

The vascular image processing apparatus may select a blood vessel tree having the highest similarity from the generated blood vessel trees. For example, the vascular image processing apparatus may calculate a similarity by calculating a degree of similarity for each of the generated blood vessel trees to the other blood vessel trees. The vascular image processing apparatus may select a blood vessel tree having the highest similarity from the generated blood vessel trees. The vascular image processing apparatus may modify the predicted vascular structure of the target vessel to match the selected blood vessel tree. For example, the vascular image processing apparatus may classify again a point that is classified into the target vessel into a branch vessel disconnected from the target vessel or a branch vessel connected to the target vessel, based on the selected blood vessel tree.

Other than the method of generating a blood vessel tree, the vascular image processing apparatus may more accurately predict the vascular structure by using the vascular image captured at a different time. Since the blood vessel dynamically moves by a cardiac impulse, blood vessels moving away from each other in the two-dimensional vascular image may be determined to be disconnected blood vessels. Accordingly, the vascular image processing apparatus may more accurately divide a disconnected blood vessel and a connected blood vessel by using a plurality of vascular images captured at different times and may modify the predicted vascular structure based on the divided result.

According to one embodiment, the vascular image processing apparatus may correct an error of the predicted vascular structure based on at least one or a combination of two or more of a diameter of the target vessel obtained from the predicted vascular structure, an endpoint direction of the target vessel obtained from the predicted vascular structure, and lesion information.

According to one embodiment, the vascular image processing apparatus may obtain information on the target vessel from the predicted vascular structure. The vascular image processing apparatus may predict a vascular region corresponding to the target vessel from the predicted vascular structure. The vascular image processing apparatus may calculate a diameter of the target vessel based on the vascular region corresponding to the predicted target vessel. The diameter of the blood vessel may decrease depending on a moving direction of the blood flow. For example, the vascular image processing apparatus may calculate the diameter of the target vessel with respect to the moving direction of the blood flow and when the diameter of the target vessel exceeds a threshold length, may determine that there is an error in the predicted vascular structure. In response to the diameter of the target vessel exceeding the threshold length, the vascular image processing apparatus may determine that there is an error in predicting the vascular structure in a partial region of the target vessel exceeding the threshold length. The vascular image processing apparatus may correct the vascular structure based on a partial region of the target vessel that is determined to include the error.

According to one embodiment, the vascular image processing apparatus may calculate an endpoint direction of the target vessel from the predicted vascular structure. The vascular image processing apparatus may correct an error of the predicted vascular structure based on the endpoint direction of the target vessel. For example, it is assumed that the target vessel is a major vessel. The endpoint of the major vessel may be usually oriented to the left side. Accordingly, the vascular image processing apparatus may determine that there is an error in the predicted vascular structure when the endpoint of the major vessel is not oriented to the left side. The vascular image processing apparatus may correct the error of the predicted vascular structure by reclassifying some points, which are classified into the branch vessel connected to the major vessel, into a region corresponding to the target vessel such that the endpoint direction of the target vessel is oriented to the left side.

According to one embodiment, the vascular image processing apparatus may correct an error of the predicted vascular structure based on lesion information. For example, the vascular image processing apparatus may predict the vascular structure to obtain information on a lesion. The information on the lesion may include information on a point where the lesion is located in the vascular structure. The vascular image processing apparatus may obtain information on the lesion from the predicted vascular structure. However, when the vascular image processing apparatus fails to obtain information on a target lesion as the target lesion is not discovered in a region corresponding to the target vessel in the predicted vascular structure, the vascular image processing apparatus may determine that there is an error in the predicted vascular structure. In this case, the vascular image processing apparatus may reassign the separate target disconnected from the existing target vessel to the target vessel. The vascular image processing apparatus may re-predict a vascular structure in the vascular image based on the reassigned target vessel and may correct the error of the previously predicted vascular structure based on the re-predicted vascular structure. For example, it is assumed that the vascular image processing apparatus predicts a vascular structure by determining the LAD to be the target vessel, however, a lesion is not detected in the LAD. In this case, the vascular image processing apparatus may predict the vascular structure again by reassigning the target vessel to the LCX, which is a different blood vessel from the LAD, and may correct the previously predicted vascular structure.

FIG. 6 illustrates a process in which the vascular image processing apparatus according to one embodiment corrects a predicted vascular structure based on a combination of two or more of a first vascular region, a second vascular region, and a third vascular region.

The vascular image processing apparatus according to one embodiment may correct an error of the predicted vascular structure in the vascular image based on a candidate separate vascular region generated by removing a region corresponding to the second vascular region from the first vascular region and a candidate branch vessel region generated by removing a region corresponding to the third vascular region from the second vascular region.

The vascular image processing apparatus may generate a candidate separate vessel region 603 by removing a region corresponding to the second vascular region from the first vascular region. The first vascular region may be a region including the target vessel, the branch vessel connected to the target vessel, and the separate vessel, and the second vascular region may be a region including the target vessel and the branch vessel connected to the target vessel. Accordingly, by removing the region corresponding to the second vascular region from the first vascular region, the candidate separate vessel region having a high probability of being classified as the separate vessel may be generated. In addition, the vascular image processing apparatus may generate a candidate branch vessel region 602 by removing the region corresponding to the third vascular region from the second vascular region. In other words, the vascular image processing apparatus may generate the candidate branch vessel region having a high probability of being classified as the branch vessel connected to the target vessel by removing the region corresponding to the third vascular region from the second vascular region.

For example, it is assumed that the vascular image processing apparatus classifies a vascular region 610 as a region corresponding to the branch vessel connected to the target vessel based on the predicted vascular structure in the vascular image. The vascular image processing apparatus may determine that there is an error in the predicted vascular structure when the vascular region 610 deviates from the candidate branch vessel region 602 and overlaps the candidate separate vessel region 603. When the vascular region 610 classified as the region corresponding to the branch vessel based on the predicted vascular structure deviates from the candidate branch vessel region 602 and overlaps the candidate separate vessel region 603 more than a threshold size, the vascular image processing apparatus may determine that there is an error in the predicted vascular structure. In this case, the vascular image processing apparatus may modify the error of the predicted vascular structure and may modify the prediction that a vascular region 611 is the region corresponding to the branch vessel. The branch vessel connected to the target vessel may often overlap with the separate vessel disconnected from the target vessel on the two-dimensional fluoroscopic image. In this case, an error in predicting the vascular structure may occur, for example, mistaking a region from an overlapping region of the branch vessel and the separate vessel to a region corresponding to the separate vessel for the branch vessel. The vascular image processing apparatus may more accurately predict the vascular structure by modifying the predicted vascular structure using the generated candidate separate vessel region 603 and the candidate branch vessel region 602.

Furthermore, the vascular image processing apparatus may predict the vascular structure of the vascular image, based on the candidate separate vascular region generated by removing a region corresponding to the second vascular region from the first vascular region and the candidate branch vessel region generated by removing a region corresponding to the third vascular region from the second vascular region. For example, the vascular image processing apparatus may predict the vascular region such that the region corresponding to the separate vessel does not overlap with the candidate branch vessel region more than the threshold region and the region corresponding to the branch vessel does not overlap with the candidate separate vessel region more than the threshold region.

Figure 7:
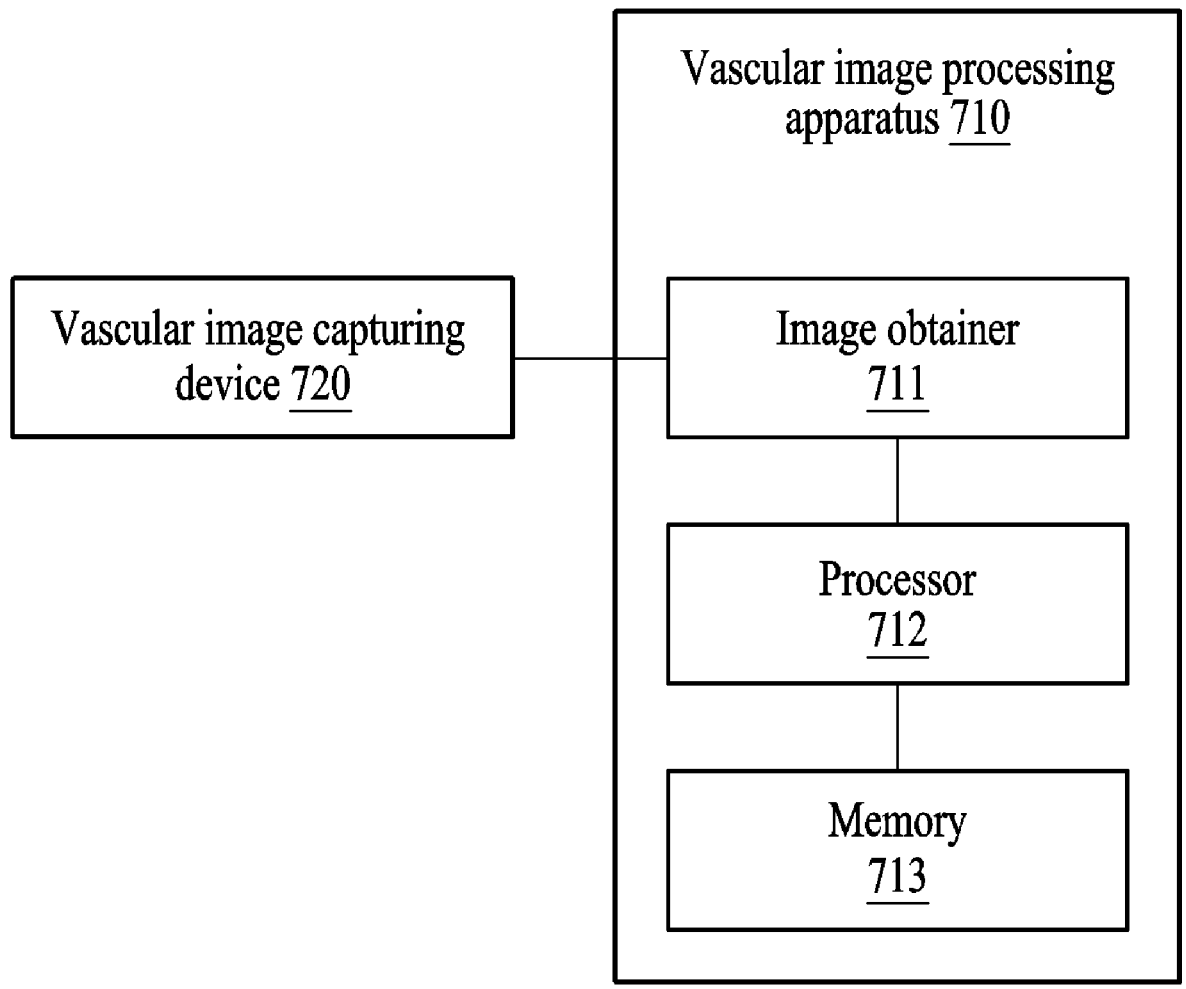
FIG. 7 is a block diagram of a vascular image processing apparatus, in accordance with an embodiment.

FIG. 7 is a block diagram schematically illustrating a vascular image processing apparatus according to one embodiment.

A vascular image processing system 700 according to one embodiment may include a vascular image processing apparatus 710 and a vascular image capturing device 720. The vascular image processing apparatus 710 may include an image obtainer 711, a processor 712, and a memory 713.

The image obtainer 711 may obtain a vascular image captured by the vascular image capturing device 720. The image obtainer 711 may obtain a vascular image from the vascular image capturing device 720 through wired/wireless data communication. However, the example is not limited thereto, and the image obtainer 711 may be integrated with the image capturing device 720.

The processor 712 may extract, from a vascular image, a first vascular region indicating the entire blood vessel included in the vascular image, a second vascular region indicating a target vessel and one or more branch vessels connected to the target vessel, and a third vascular region indicating the target vessel. In addition, the processor 712 may predict a vascular structure from the vascular image, based on the first vascular region, the second vascular region, and the third vascular region, which are extracted from the vascular image. In other words, the processor 712 may predict the vascular structure by predicting vascular regions by dividing a phase into the target vessel, the target vessel and the branch vessel connected to the target vessel, and the separate vessel disconnected from the target vessel. In addition, the processor 712 may perform operations described with reference to FIGS. 1 through 6.

The memory 713 may store the vascular image obtained by the vascular image capturing device 720. In addition, the memory 713 may store the first vascular region, the second vascular region, and the third vascular region in the vascular image.

The examples described herein may be implemented using hardware components, software components and/or combinations thereof. A processing apparatus may be implemented using one or more general-purpose or special-purpose computers, such as, for example, a processor, a controller and an arithmetic logic unit (ALU), a DSP, a microcomputer, an FPGA, a programmable logic unit (PLU), a microprocessor or any other device capable of responding to and executing instructions in a defined manner. The processing apparatus may run an operating system (OS) and one or more software applications that run on the OS. The processing apparatus also may access, store, manipulate, process, and create data in response to execution of the software. For purpose of simplicity, the description of a processing apparatus is used as singular; however, one skilled in the art will appreciate that a processing apparatus may include multiple processing elements and multiple types of processing elements. For example, the processing apparatus may include a plurality of processors, or a single processor and a single controller. In addition, different processing configurations are possible, such as parallel processors.

The software may include a computer program, a piece of code, an instruction, or some combination thereof, to independently or uniformly instruct or configure the processing apparatus to operate as desired. Software and data may be embodied permanently or temporarily in any type of machine, component, physical or pseudo equipment, computer storage medium or device, or in a propagated signal wave capable of providing instructions or data to or being interpreted by the processing apparatus. The software also may be distributed over network-coupled computer systems so that the software is stored and executed in a distributed fashion. The software and data may be stored by one or more non-transitory computer-readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher-level code that may be executed by the computer using an interpreter.

The above-described devices may be configured to act as one or more software modules in order to perform the operations of the above-described examples, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

Accordingly, other implementations are within the scope of the following claims.

The invention claimed is:

1. A vascular image processing method performed by a processor comprising:
   extracting a first vascular region which is a region including a target vessel, a branch vessel connected to the target vessel, and a separate vessel disconnected from the target vessel, a second vascular region which is a region including the target vessel and the branch vessel connected to the target vessel, and a third vascular region which is a region including the target vessel from a vascular image; and
   predicting a vascular structure in the vascular image, based on the first vascular region, the second vascular region, and the third vascular region, which are extracted from the vascular image;
   wherein the predicting of the vascular structure comprises predicting a region corresponding to the target vessel in the vascular image by overlapping the first vascular region, the second vascular region, and the third vascular region with each other.

2. The vascular image processing method of claim 1, wherein the predicting of the vascular structure comprises classifying each point corresponding to a blood vessel in the vascular image into the target vessel, the one or more branch vessels connected to the target vessel, and a separate vessel disconnected from the target vessel.

3. The vascular image processing method of claim 1, wherein the extracting comprises:
   extracting the first vascular region prior to extraction of the second vascular region and the third vascular region;
   extracting, from the first vascular region, a cross region comprising at least one of a region comprising a branch point where a branch vessel branches off and a region where different blood vessels overlap with each other; and
   extracting the second vascular region and the third vascular region from the vascular image, based on the extracted cross region.

4. The vascular image processing method of claim 1, further comprising:
   correcting an error of a predicted vascular structure in the vascular image.

5. The vascular image processing method of claim 4, wherein the correcting of the error of the predicted vascular structure comprises:
   obtaining another vascular image captured at a different time from the vascular image; and
   correcting the error of the predicted vascular structure in the vascular image, based on a comparison result of the predicted vascular structure in the vascular image and a predicted vascular structure in the other obtained vascular image.

6. The vascular image processing method of claim 4, wherein the correcting of the error of the predicted vascular structure comprises correcting the error of the predicted vascular structure based on at least one or a combination of two or more of a diameter of a target vessel obtained from the predicted vascular structure, an endpoint direction of the target vessel obtained from the predicted vascular structure, and lesion information.

7. The vascular image processing method of claim 4, wherein the correcting of the error of the predicted vascular structure comprises correcting the error of the predicted vascular structure in the vascular image, based on a candidate separate vessel region generated by removing a region corresponding to the second vascular region from the first vascular region and a candidate branch vessel region generated by removing a region corresponding to the third vascular region from the second vascular region.

8. A non-transitory computer-readable storage medium storing instructions that, when executed by a processor, cause the processor to perform the method comprising the steps of:
   extracting a first vascular region which is a region including a target vessel, a branch vessel connected to the target vessel, and a separate vessel disconnected from the target vessel, a second vascular region which is a region including the target vessel and the branch vessel connected to the target vessel, and a third vascular region which is a region including the target vessel from a vascular image; and
   predicting a vascular structure in the vascular image, based on the first vascular region, the second vascular region, and the third vascular region, which are extracted from the vascular image;
   wherein the predicting of the vascular structure comprises predicting a region corresponding to the target vessel in the vascular image by overlapping the first vascular region, the second vascular region, and the third vascular region with each other.

9. A vascular image processing apparatus comprising:
   an image obtainer configured to obtain a vascular image; and
   a processor configured to extract a first vascular region which is a region including a target vessel, a branch vessel connected to the target vessel, and a separate vessel disconnected from the target vessel, a second vascular region which is a region including the target vessel and the branch vessel connected to the target vessel, and a third vascular region which is a region including the target vessel and predict a vascular structure in the vascular image, based on the first vascular region, the second vascular region, and the third vascular region, which are extracted from the vascular image from a vascular image, and predict a vascular structure in the vascular image, based on the first vascular region, the second vascular region, and the third vascular region, which are extracted from the vascular image, wherein the processor is configured to predict a region corresponding to the target vessel in the vascular image by overlapping the first vascular region, the second vascular region, and the third vascular region with each other.

10. The vascular image processing apparatus of claim 9, wherein the processor is configured to classify each point corresponding to a blood vessel in the vascular image into the target vessel, the one or more branch vessels connected to the target vessel, and a separate vessel disconnected from the target vessel.

11. The vascular image processing apparatus of claim 9, wherein the processor is configured to extract the first vascular region prior to extraction of the second vascular region and the third vascular region, extract, from the first vascular region, a cross region comprising at least one of a region comprising a branch point where a branch vessel branches off and a region where different blood vessels overlap with each other, and extract the second vascular region and the third vascular region from the vascular image, based on the extracted cross region.

12. The vascular image processing apparatus of claim 9, wherein the processor is configured to correct an error of a predicted vascular structure in the vascular image.

13. The vascular image processing apparatus of claim 12, wherein the processor is further configured to obtain another vascular image captured at a different time from the vascular image and correct the error of the predicted vascular structure in the vascular image, based on a comparison result of the predicted vascular structure in the vascular image and a predicted vascular structure in the other obtained vascular image.

14. The vascular image processing apparatus of claim 12, wherein the processor is further configured to correct the error of the predicted vascular structure based on at least one or a combination of two or more of a diameter of a target vessel obtained from the predicted vascular structure, an endpoint direction of the target vessel obtained from the predicted vascular structure, and lesion information.

15. The vascular image processing apparatus of claim 12, wherein the processor is further configured to correct the error of the predicted vascular structure in the vascular image, based on a candidate separate vessel region generated by removing a region corresponding to the second vascular region from the first vascular region and a candidate branch vessel region generated by removing a region corresponding to the third vascular region from the second vascular region.

* * * * *